United States Patent
Granier et al.

(10) Patent No.: US 12,378,214 B2
(45) Date of Patent: Aug. 5, 2025

(54) 12-OXASPIRO[5,5]UNDEC-8-ENE USEFUL IN FRAGRANCE COMPOSITIONS

(71) Applicant: Givaudan SA, Vernier (CH)

(72) Inventors: Thierry Granier, Duebendorf (CH); Daniel Bieri, Zurich (CH); Gerhard Brunner, Opfikon (CH); Sandro Dossenbach, Gossau (CH); Heinz Koch, Baeretswil (CH)

(73) Assignee: Givaudan SA, Vernier (CH)

( * ) Notice: Subject to any disclaimer, the term of this patent is extended or adjusted under 35 U.S.C. 154(b) by 770 days.

(21) Appl. No.: 17/615,301

(22) PCT Filed: Jun. 3, 2020

(86) PCT No.: PCT/EP2020/065267
§ 371 (c)(1),
(2) Date: Nov. 30, 2021

(87) PCT Pub. No.: WO2020/245142
PCT Pub. Date: Dec. 10, 2020

(65) Prior Publication Data
US 2022/0220091 A1      Jul. 14, 2022

(30) Foreign Application Priority Data
Jun. 5, 2019   (GB) ................................. 1907995

(51) Int. Cl.
*C07D 311/96*    (2006.01)
*A61K 8/49*      (2006.01)
*A61Q 13/00*     (2006.01)
*C11B 9/00*      (2006.01)

(52) U.S. Cl.
CPC .......... *C07D 311/96* (2013.01); *A61K 8/498* (2013.01); *A61Q 13/00* (2013.01); *C11B 9/0088* (2013.01)

(58) Field of Classification Search
CPC ...... C07D 311/96; A61K 8/498; A61Q 13/00; C11B 9/0088; C11D 3/50
USPC ...................................................... 549/331
See application file for complete search history.

(56) References Cited

U.S. PATENT DOCUMENTS

| 4,186,103 A      | 1/1980 | Hall et al. |
| 2004/0072721 A1  | 4/2004 | Vial et al. |

FOREIGN PATENT DOCUMENTS

WO         2010125100 A1      11/2010

OTHER PUBLICATIONS

F. Shahidi edited, Li Jie and Zhu Guobin translated, "Flavors of Meat and Aquatic Products, 2nd Edition", China Light Industry Press, Aug. 31, 2001, pp. 309-310.
International Search Report for Application No. PCT/EP2020/065267 dated Jul. 9, 2020.
Written Opinion for Application No. PCT/EP2020/065267 dated Jul. 9, 2020.
Great Britain Search Report for Application No. 1907995.3 dated Nov. 20, 2019.
Yue Zou, et al., Organocatalytic Multicomponent a-Methylenation/Diels-Alder Reactions: A Versatile Route to Substituted Cyclohexenecarbaldehyde Derivatives, Chemistry Europe, European Chemical Societies Publishing, May 29, 2008, pp. 5335-5345, vol. 14, Issue 17, Wiley InterScience.
V. Bardarov, et al., Comparison of the Chiral Selectivity of Two GC Columns for the Separation of Enantiomers in Rose Oil, Journal of the University of Chemical Technology and Metallurgy, Jul. 12, 2011, pp. 320-328, vol. 46, Issue 3.
Elisabetta Brenna, et al., Enantioselective perception of chiral odorants, Tetrahedron: Asymmetry, Jan. 6, 2003, pp. 1-42, vol. 14, Issue 1, Elsevier Science, Ltd.

*Primary Examiner* — Taylor V Oh
(74) *Attorney, Agent, or Firm* — Curatolo Sidoti & Trillis Co., LPA; Floyd Trillis, III; Salvatore A. Sidoti

(57) ABSTRACT

A compound according to formula (−)-(Id*)

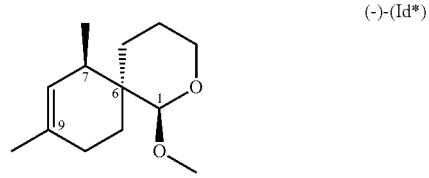

(−)-(Id*)

wherein the compound shows negative specific rotation values,
and it's use as fragrance.

21 Claims, No Drawings

12-OXASPIRO[5.5]UNDEC-8-ENE USEFUL IN FRAGRANCE COMPOSITIONS

CROSS REFERENCE TO RELATED APPLICATIONS

This application is a national stage application of International Application No. PCT/EP2020/065267, filed 3 Jun. 2020, which claims priority from Great Britain Application No. 1907995.3, filed 5 Jun. 2019, both of which applications are incorporated herein by reference.

The present invention is directed to a novel organic compound, a method of preparing said compound and its use as fragrance ingredient. The invention also relates to perfume compositions and to articles, such as fine fragrances or consumer product compositions perfumed by the compound, or the perfume compositions containing said compound.

BACKGROUND OF THE INVENTION

Conventionally, compounds having grapefruit and cassis characteristics have been selected from sulphur-containing organic compounds, such as Corps Cassis®, Corps Pamplemousse® and 1-p-Menthene-8-thiol (Grapefruit mercaptane), and non-sulphur-containing organic compounds such as Buccoxime®, Theaspiran and Etaspiren®. However, the use of known non-sulphur compounds is expensive, and the sulphur-containing compounds tend to be unstable in various applications and may cause unpleasant off-odors.

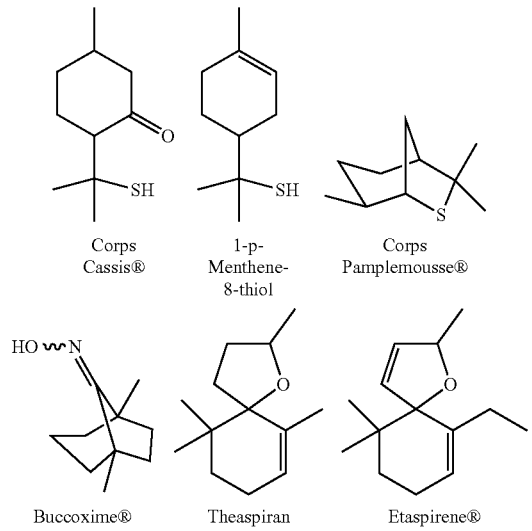

Corps Cassis®    1-p-Menthene-8-thiol    Corps Pamplemousse®

Buccoxime®    Theaspiran    Etaspirene®

In WO2010125100A1 a group of 1-alkoxy-2-oxaspiro[5.5]undec-8-enes was described to constitute new grapefruit and cassis odorants, and thus to be a group of valuable new ingredients for the flavour and fragrance industry. One example, amongst others, is 1-methoxy-7,9-dimethyl-2-oxaspiro[5.5]undec-8-ene with a green, fruity, floral, cassis, grapefruit odour.

DESCRIPTION OF THE INVENTION 1-methoxy-7,9-dimethyl-2-oxaspiro[5.5]undec-8-ene (compound of formula (I)) is a compound with three stereocenters, and therefore, there are 8 stereoisomers of said compound in total.

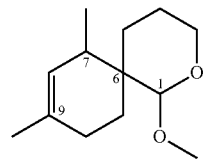
(I)

They form four different diastereoisomers, each of which is a pair of two enantiomers.

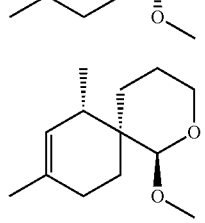
(±)-(Ia*)

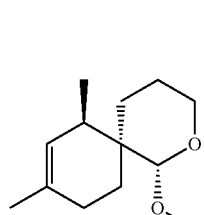
(±)-(Ib*)

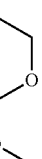

(±)-(Ic*)

(±)-(Id*)

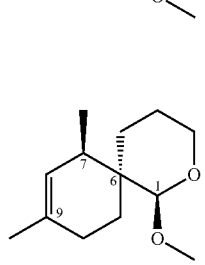

Surprisingly, it was now found that the perfumistic benefit of the compound of formula (I) depends on the stereochemistry: only one diastereoisomer (±)-(Id*) out of four is a strong odourant, while the others show only very weak odourant properties, if any.

The compound according to formula (±)-(Id*) is a racemate, a 1:1 mixture of two enantiomers. Deeper analysis revealed that only one of those two enantiomers is olfactorily active. The two enantiomers have been separated by chiral columns, and the olfactorily active one shows negative specific rotation values.

So in a first aspect of the invention, there is provided a compound according to formula (−)-(Id*), wherein the compound shows negative specific rotation values ((−)-(1R*, 6R*,7R*)-1-methoxy-7,9-dimethyl-2-oxaspiro[5.5]undec-8-ene). The absolute configuration of said compound has not been solved. Said compound has a strong cassis, grapefruit, fruity, juicy odour.

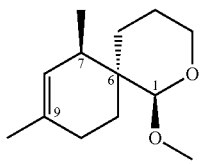

(−)-(Id*)

In a further aspect of the invention, there is provided an isomeric mixture comprising the compound according to formula (−)-(Id*) and the compound according to formula (+)-(Id*).

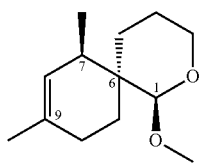

(+)-(Id*)

In a certain embodiment, the isomeric mixture comprises the compound according to formula (−)-(Id*) and the compound according to formula (+)-(Id*) in a 1:1 weight ratio, which is a racemic mixture (±)-(Id*) of the two enantiomers.

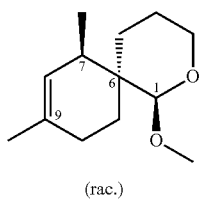

(±)-(Id*)

(rac.)

In another embodiment, the isomeric mixture can be enriched in one of the two enantiomers, preferably enriched in enantiomer (−)-(Id*). The weight ratio of the compound according to formula (+)-(Id*) to the compound according to formula (+)-(Id*) in the composition may range from about 99.99:0.01: to about 1:99, for example from about 99.9:0.1 to about 5:95.

In general, formula (±)-(Id*) and the formulae of the other stereoisomers, are indicating the relative but not the absolute configuration at the ring system, as indicated by "*". The diastereoisomers of the present invention are to be understood as mixtures of enantiomers, as indicated by the prefix "(±)-" or "rac-". Pure enantiomers are indicated by the prefix "(+)-" or "(−)-".

If a compound exists in the form of different stereoisomers, it might be used as a mixture. Alternatively, it may be resolved in groups of diastereoisomers or as pure stereoisomers. Resolving stereoisomers adds to the complexity of manufacture and purification of the compound, and so it is preferred to use the compound as mixture of its stereoisomers simply for economic reasons. However, if it is desired to prepare individual stereoisomers, this may be achieved according to methods known in the art, e.g. stereoselective synthesis, preparative HPLC and GC.

In one aspect of the invention, the compound of formula (±)-(Id*) is provided in highly enriched or essentially pure form, with low amounts or essentially free of the corresponding diastereoisomers (±)-(Ia*), (±)-(Ib*) and/or (±)-(Ic*). That means that the preferred diastereoisomer (±)-(Id*) is present in at least 90 weight %, particularly in at least 95 weight %, more particularly in at least 98 weight %, even more particularly in 99 weight % or higher.

In another aspect of the invention, a diastereoisomeric mixture is provided, comprising a relatively high amount of the preferred diastereoisomer according to formula (±)-(Id*) along with the other diastereoisomers (±)-(Ia*), (±)-(Ib*) and/or (±)-(Ic*) in lower amounts. That means that the preferred diastereoisomer (±)-(Id*) is present in at least 50 weight %, particularly in at least 60 weight %, more particularly in at least 70 weight %, even more particularly in 80 weight % or higher.

In a further aspect of the invention, there is provided a use as fragrance of a compound according to formula (−)-(Id*) or according to formula (±)-(Id*).

In yet another aspect of the present invention, there is provided a perfume composition comprising a compound according to formula (−)-(Id*) or according to formula (±)-(Id*).

The compounds of the invention may be used alone, or in combination with known odorant molecules selected from the extensive range of natural products, and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odorants in perfume compositions, for example, carrier materials, and other auxiliary agents commonly used in the art.

As used herein, "carrier material" means a material which is practically neutral from a odorant point of view, i.e. a material that does not significantly alter the organoleptic properties of odorants.

The term "auxiliary agent" refers to ingredients that might be employed in a perfume composition for reasons not specifically related to the olfactive performance of said composition. For example, an auxiliary agent may be an ingredient that acts as an aid to processing a fragrance ingredient or ingredients, or a composition containing said ingredient(s), or it may improve handling or storage of a fragrance ingredient or composition containing same. It might also be an ingredient that provides additional benefits such as imparting color or texture. It might also be an ingredient that imparts light resistance or chemical stability to one or more ingredients contained in a perfume composition. A detailed description of the nature and type of adjuvants commonly used in perfume compositions containing same cannot be exhaustive, but it has to be mentioned that said ingredients are well known to a person skilled in the art.

As used herein, "perfume composition" means any composition comprising the compound of formula (I) and a base material, e.g. a diluent conventionally used in conjunction with odorants, such as diethyl phthalate (DEP), dipropylene glycol (DPG), isopropyl myristate (IPM), pentane-1,2-diol, triethyl citrate (TEC) and alcohol (e.g. ethanol). Optionally, the composition may comprise an anti-oxidant adjuvant. Said anti-oxidant may be selected from Tinogard® TT (BASF), Tinogard® Q (BASF), Tocopherol (including its isomers, CAS 59-02-9; 364-49-8; 18920-62-2; 121854-78-2), 2,6-bis(1,1-dimethylethyl)-4-methylphenol (BHT, CAS 128-37-0) and related phenols, hydroquinones (CAS 121-31-9).

The following list comprises examples of known odorant molecules, which may be combined with the compound according to formula (−)-(Id*) or according to formula (±)-(Id*):

essential oils and extracts, e.g. castoreum, costus root oil, oak moss absolute, geranium oil, tree moss absolute, basil oil, fruit oils, such as bergamot oil and mandarine oil, myrtle oil, palmarose oil, patchouli oil, petitgrain oil, jasmine oil, rose oil, sandalwood oil, wormwood oil, lavender oil and/or ylang-ylang oil;

alcohols, e.g. cinnamic alcohol ((E)-3-phenylprop-2-en-1-ol); cis-3-hexenol ((Z)-hex-3-en-1-ol); citronellol (3,7-dimethyloct-6-en-1-ol); dihydro myrcenol (2,6-dimethyloct-7-en-2-ol); Ebanol™ ((E)-3-methyl-5-(2,2,3-trimethylcyclopent-3-en-1-yl)pent-4-en-2-ol); eugenol (4-allyl-2-methoxyphenol); ethyl linalool ((E)-3,7-dimethylnona-1,6-dien-3-ol); farnesol ((2E,6Z)-3,7,11-trimethyldodeca-2,6,10-trien-1-ol); geraniol ((E)-3,7-dimethylocta-2,6-dien-1-ol); Super Muguet™ ((E)-6-ethyl-3-methyloct-6-en-1-ol); linalool (3,7-dimethylocta-1,6-dien-3-ol); menthol (2-isopropyl-5-methylcyclohexanol); Nerol (3,7-dimethyl-2,6-octadien-1-ol); phenyl ethyl alcohol (2-phenylethanol); Rhodinol™ (3,7-dimethyl-6-en-1-ol); Sandalore™ (3-methyl-5-(2,2,3-trimethylcyclopent-3-en-1-yl)pentan-2-ol); terpineol (2-(4-methylcyclohex-3-en-1-yl)propan-2-ol); or Timberol™ (1-(2,2,6-trimethylcyclohexyl)hexan-3-ol); 2,4,7-trimethylocta-2,6-dien-1-ol, and/or [1-methyl-2(5-methylhex-4-en-2-yl)cyclopropyl]-methanol;

aldehydes and ketones, e.g. anisaldehyde (4-methoxybenzaldehyde); alpha amyl cinnamic aldehyde (2-benzylideneheptanal); Georgywood™ (1-(1,2,8,8-tetramethyl-1,2,3,4,5,6,7,8-octahydronaphthalen-2-yl) ethanone); Hydroxycitronellal (7-hydroxy-3,7-dimethyloctanal); Iso E Super® (1-(2,3,8,8-tetramethyl-1,2,3,4,5,6,7,8-octahydronaphthalen-2-yl) ethanone); Isoraldeine® ((E)-3-methyl-4-(2,6,6-trimethylcyclohex-2-en-1-yl)but-3-en-2-one); Hedione® (methyl 3-oxo-2-pentylcyclopentaneacetate); 3-(4-isobutyl-2-methylphenyl)propanal; maltol; methyl cedryl ketone; methylionone; verbenone; and/or vanillin;

ether and acetals, e.g. Ambrox® (3a,6,6,9a-tetramethyl-2,4,5,5a,7,8,9,9b-octahydro-1H-benzo[e][1]benzofuran); geranyl methyl ether ((2E)-1-methoxy-3,7-dimethylocta-2,6-diene); rose oxide (4-methyl-2-(2-methylprop-1-en-1-yl)tetrahydro-2H-pyran); and/or Spirambrene® (2',2',3,7,7-pentamethylspiro[bicyclo[4.1.0]heptane-2,5'-[1,3]dioxane]);

esters and lactones, e.g. benzyl acetate; cedryl acetate ((1S,6R,8aR)-1,4,4,6-tetramethyloctahydro-1H-5,8a-methanoazulen-6-yl acetate); γ-decalactone (6-pentyltetrahydro-2H-pyran-2-one); Helvetolide® (2-(1-(3,3-dimethylcyclohexyl)ethoxy)-2-methylpropyl propionate); γ-undecalactone (5-heptyloxolan-2-one); and/or vetiveryl acetate ((4,8-dimethyl-2-propan-2-ylidene-3,3a,4,5,6,8a-hexahydro-1H-azulen-6-yl) acetate);

macrocycles, e.g. Ambrettolide ((Z)-oxacycloheptadec-10-en-2-one); ethylene brassylate (1,4-dioxacycloheptadecane-5,17-dione); and/or Exaltolide® (16-oxacyclohexadecan-1-one); and heterocycles, e.g. isobutylquinoline (2-isobutylquinoline).

In yet another aspect of the present invention, there is provided a perfumed article, such as a fine fragrance or a personal or household care product, perfumed with a compound according to formula (−)-(Id*) or according to formula (±)-(Id*).

The compound according to formula (−)-(Id*) or according to formula (±)-(Id*) may be used in a broad range of perfumed articles, e.g. in any field of fine and functional perfumery, such as perfumes, air care products, household products, laundry products, body care products and cosmetics. The compound can be employed in widely varying amounts, depending upon the specific article and on the nature and quantity of other odorant ingredients. The proportion is typically from 0.0001 to 3 weight percent of the article. In one embodiment, the compound of the present invention may be employed in a fabric softener in an amount from 0.001 to 0.3 weight percent (e.g. 0.01 to 0.1 including 0.05 weight %). In another embodiment, the compound according to formula (−)-(Id*) or according to formula (±)-(Id*) may be used in fine perfumery in amounts from 0.001 to 30 weight percent (e.g. up to about 10 or up to 20 weight percent), more preferably between 0.01 and 5 weight percent. However, these values are given only by way of example, since the experienced perfumer may also achieve effects or may create novel accords with lower or higher concentrations.

In one embodiment there is provided a perfumed article comprising an acceptable amount of compound according to formula (−)-(Id*) or according to formula (±)-(Id*). For example, the fragranced article may comprise 0.000001 weight % to 90 weight % (including 0.00001 weight %; 0.0001 weight %, 0.001 weight %, 0.01 weight %, 0.05 weight %, 0.1 weight %, 0.5 weight %, 1 weight %, 5 weight %, 8 weight %, 10 weight %, 15 weight %, 20 weight %, 25 weight %, 30 weight %, 50 weight %, 60 weight %, 65 weight %) based on the total amount of the article.

The compound according to formula (−)-(Id*) or according to formula (±)-(Id*) may be employed in a consumer product base simply by directly mixing the compound of the present invention, or a perfume composition comprising the compound according to formula (−)-(Id*) or according to formula (±)-(Id*), or a mixture thereof, with the consumer product base, or it may, in an earlier step, be entrapped with an entrapment material, for example, polymers, capsules, microcapsules and nanocapsules, liposomes, film formers, absorbents such as carbon or zeolites, cyclic oligosaccharides and mixtures thereof, and then mixed with the consumer product base.

Thus, the invention additionally provides a method of manufacturing a perfumed article, comprising the incorporation of a compound according to formula (−)-(Id*) or according to formula (±)-(Id*), as a fragrance ingredient, either by directly admixing the compound to the consumer product base or by admixing a perfume composition comprising the compound according to formula (−)-(Id*) or according to formula (±)-(Id*), which may then be mixed with a consumer product base, using conventional techniques and methods. Through the addition of an olfactory acceptable amount of the compound of the present invention as hereinabove described the odor notes of a consumer product base will be improved, enhanced, or modified.

Thus, the invention furthermore provides a method to confer, enhance, improve or modify the hedonic properties of a perfume composition or a consumer product, which method comprises adding to said perfume composition or consumer product a compound according to formula (−)-(Id*) or according to formula (±)-(Id*).

As used herein, "consumer product base" means a composition for use as a consumer product to fulfill specific actions, such as cleaning, softening, and caring or the like. Examples of such products include fine perfumery, e.g. perfume and eau de toilette; fabric care, household products and personal care products such as cosmetics, laundry care detergents, rinse conditioner, personal cleansing composition, detergent for dishwasher, surface cleaner, laundry products, e.g. softener, bleach, detergent; body-care products, e.g. shampoo, shower gel; air care products (includes products that contain preferably volatile and usually pleasant-smelling compounds which advantageously can even in very small amounts mask unpleasant odors). Air fresheners for living areas contain, in particular, natural and synthetic essential oils such as pine needle oils, citrus oil, eucalyptus oil, lavender oil, and the like, in amounts for example of up to 50% by weight. As aerosols they tend to contain smaller amounts of such essential oils, by way of example less than 5% or less than 2% by weight, but additionally include compounds such as acetaldehyde (in particular, <0.5% by weight), isopropyl alcohol (in particular, <5% by weight), mineral oil (in particular, <5% by weight), and propellants.

Cosmetic Products Include:

(a) cosmetic skincare products, especially bath products, skin washing and cleansing to products, skincare products, eye makeup, lip care products, nail care products, intimate care products, foot care products;

(b) cosmetic products with specific effects, especially sunscreens, tanning products, de-pigmenting products, deodorants, antiperspirants, hair removers, and shaving products;

(c) cosmetic dental-care products, especially dental and oral care products, tooth care products, cleaners for dental prostheses, adhesives for dental prostheses; and (d) cosmetic hair care products, especially hair shampoos, hair care products, hair setting products, hair-shaping products, and hair coloring products.

The compound of formula (I) may be prepared by reaction of the corresponding hemiacetal of formula (II) with the corresponding alcohol $R^1OH$ in the presence of a catalytic amount of an acid catalyst under conditions known to the person skilled in the art, as shown in scheme 1 below. The preparation of the hemiacetal of formula (II) is described e.g. by Yue Zou et al. (Chem. Eur. J. 2008, 14, 5335-5345).

Scheme 1

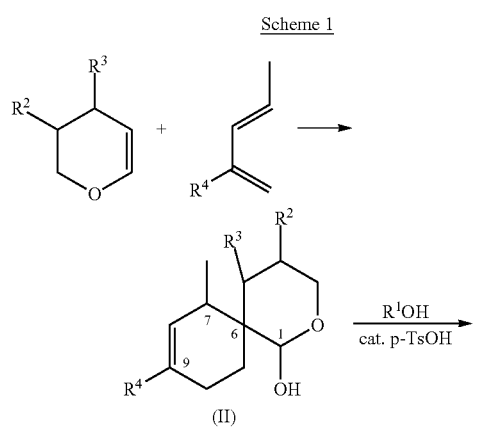

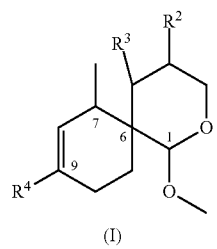

By varying the conditions of the acetalization of the hemiacetal of formula (II) to the compound of formula (I) (second step) the ratio of the diastereoisomers can be controlled. A relatively high amount of acids and longer reaction time lead to mixtures enriched (up to 75%) in diastereoisomer (±)-(Id*). On the other hand, shorter reaction times lead to higher proportions of diastereoisomer (±)-(Ic*).

The separation of the stereoisomers may be achieved by different chromatography techniques, using chiral and/or achiral stationary phases.

The present invention is now further described by the following, non-limiting examples.

EXAMPLES

Example 1: Preparation of the Stereoisomers of Compound of Formula (I)

Hemiacetal 7,9-dimethyl-2-oxaspiro[5.5]undec-8-en-1-ol was obtained according to Yue Zou et al. (Chem. Eur. J. 2008, 14, 5335-5345). The crude product 7,9-dimethyl-2-oxaspiro[5.5]undec-8-en-1-ol (233 g, 50.969 mol, 81.8% purity) was combined with methanol (156 g, 4.865 mol, 5 eq., Fluka), toluene (30 ml, Honeywell) and aq. sulfuric acid (11.81 g, 0.117 mol, 97%, 0.12 eq.). The resulting mixture was immersed in an oil bath preheated at 85° C., refluxed (65° C.) for one hour, cooled to RT, transferred into a separation funnel, diluted with MTBE (100 ml, technical) and treated with aq. saturated sodium carbonate solution (200 ml, resulting pH 8). The separated aqueous phase was extracted three times with MTBE (100 ml). The combined organic phases were washed with aq. saturated NaCl (100 ml) to neutrality, dried over $MgSO_4$, filtered and the filtrate concentrated on rotavapor (55° C., 80 mbar) and under HV (20° C., 0.08 mbar) giving 195.6 g of a brown oil (GC-purity: 99%).

The obtained product (I) is a racemic mixture of four diastereomers ((±)-(Ia*), (±)-(Ib*), (±)-(Ic*), (±)-(Id*)), each diastereomer being present as a 50:50 mixture of enantiomers (e.g. for (±)-(Ia*): (−)-(Ia*)/(+)-(Ia*)). The ratio of the diastereoisomers (±)-(Ia*):(±)-(Ib*):(±)-(Ic*):(±)-(Id*) is 3:8:15:74 (determined by $^1$H-NMR on the ratio of the anomeric signals at C1).

Example 2: Separation of the Stereoisomers of Compound of Formula (I)

GC-sniff of the obtained product (I) showed that only one diastereomer is olfactorily active. More specially, as the best separation was obtained using chiral GC columns, it was found that only one of the eight optically active diastereomers was olfactorily active.

The minor isomers (±)-(Ia*) and (±)-(Ib*) are well separated from the major isomers (±)-(Ic*) and (±)-(Id*) using an achiral column (ZB-wax), and the coeluted mixture of (±)-(Ia*) and (±)-(Ib*) was found odorless.

Good separation was obtained using the chiral GC column Hydrodex-beta-3-P: there was coelution of one enantiomer of (±)-(Ia*) and one enantiomer of (±)-(Ic*) only. The elution sequence is as follows: ((Ia*)(Ic*)), (Ib*), (Ic*)', (Ib*)', (Ia*)', (Id*), (Id*)', and only the slowest eluting enantiomer of (Id*) is olfactorily active.

Details of the Separation:

Chiral GC method (Thermo Scientific Trace 1310 GC & TriPlus 100LS Autosampler): split ratio 1:1 between FID (FrontDetector) & sniffing port (A2D), 1 µl (10000 ng/µl in MtBE), split 20:1, hot needle injection technique, injector 210° C., carrier gas $H_2$, constant flow 1.5 ml/min, column 25 m×0.25 mm Hydrodex-beta-3P (Macherey-Nagel, P/N 723358.25, S/N 20114/61), temperature program 2 min@50° C.-2° C./min-2 min@190° C., FID base 230° C., air 350 ml/min, $H_2$ 35 ml/min, $N_2$ make-up 40 ml/min, Chromeleon 7.2.

On a preparative scale, the separation of the main stereoisomers (+)-(Id*) and (−)-(Id*) was achieved by supercritical fluid chromatography (SFC):

Around 19 g of (I) was dissolved in 190 mL methanol (Merck, HPLC grade) and submitted (230 injections, injection volume of 1 ml) to SFC using a PIC 10-150 with UV detector at 210 nm equipped with a Phenomenex Lux A1 (30×250 mm, 5 µm) column held at 35° C., applying a flow rate of 3 ml/min. Elution (mobile phases: A: 90% SFC grade carbon dioxide, B: Methanol (Merck HPLC grade); isocratic, flow rate 100 ml/min) and collection of the fractions at room temperature led to two fractions: F1 (~2.0 l) and F2 (~2.2 l) that were concentrated (35° C., 560 mbar) giving around 4.0 g of the separated fractions. F2 consisted of (+)-(Id*), the olfactively inactive enantiomer of the main diastereomeric pair of (I), while F1 consisted of a mixture of the remaining stereoisomers except (+)-(Id*).

Semi-Prep. HPLC Separation:

The fraction F1, obtained by SFC, diluted 200 mg/ml in MeOH (Fisher Scientific, M/4000/15), was submitted to semi-prep. HPLC using a Thermo Scientific Ultimate 3000 HPLC system equipped with Chromeleon 7.2 CDS software and a DAD detector (UV detection at 210 nm, with an injection volume of 1.6 µl, 110 injections), deploying a Merck LichroCART-ChiraDex column (4×250 mm, 5 µm) cooled to 6° C., applying a flow rate of 0.6 ml/min of purified water/MeOH, 25:75% v/v, isocratic elution.

Solid Phase Extraction (SPE):

After conditioning the cartridge (Waters Oasis HLB 6 cc cartridge, 186000115) with 5 mL MtBE (VWR, 2.2105.320), 5 mL MeOH and 5 ml purified water:MeOH 90:10% v/v, the pooled fractions obtained by LC prep. were diluted with 900 mL purified water and applied at a flow rate of ca. 5.5 h/l onto the cartridge. After washing with 50 ml purified water, the cartridge was flushed with a syringe piston and dried under vacuum for 15 min. The elution was performed with 4 times 2 ml MtBE. The eluates were pooled and the phases separated. Drying of the MtBE phase over two $Na_2SO_4$ syringe cartridges (Chromafix Dry/$Na_2SO_4$, 250 mg, 731852), flushed twice with 0.5 ml MtBE led, after solvent evaporation under a $N_2$ stream at room temperature, to 13 mg of (−)-(Id*) (GC: 94% purity).

(±)-(Ia*): (±)-(1S*,6R*,7S*)-1-methoxy-7,9-dimethyl-2-oxaspiro[5.5]undec-8-ene $^1$H-NMR (600 MHz, $C_6D_6$): δ (selected signals) 5.33-5.30 (m, 1H), 4.55 (s, 1H), 3.72-3.67 (m, 1H), 3.48-3.43 (m, 1H), 3.25 (s, 3H), 2.72-2.66 (m, 1H), 1.59 (s, 3H), 0.86 (dd, J=7.2, 3H). $^{13}$C-NMR (150 MHz, $C_6D_6$): δ 132.4 (s), 126.9 (d), 101.5 (d), 59.4 (t), 54.9 (q), 37.2 (s), 32.3 (d), 27.5 (t), 27.1 (t), 26.9 (t), 23.5 (q), 21.6 (t), 15.8 (q).

(±)-(Ib*): (±)-(1R*,6R*,7S*)-1-methoxy-7,9-dimethyl-2-oxaspiro[5.5]undec-8-ene $^1$H-NMR (600 MHz, $C_6D_6$): δ (selected signals) 5.33-5.30 (m, 1H), 4.49 (s, 1H), 3.71-3.66 (m, 1H), 3.50-3.46 (m, 1H), 3.23 (s, 3H), 2.50-2.44 (m, 1H), 1.57 (s, 3H), 0.93 (dd, J=7.2, 3H). $^{13}$C-NMR (150 MHz, $C_6D_6$): δ 131.3 (s), 127.2 (d), 101.9 (d), 58.4 (t), 54.7 (q), 36.9 (s), 34.7 (d), 27.0 (t), 25.9 (t), 24.4 (t), 23.4 (q), 21.4 (t), 16.9 (q).

(±)-(Ia*) and (±)-(Ib*)

GC-MS (EI): 210 (8), 195 (2), 179 (9), 178 (26), 163 (18), 150 (15), 135 (14), 122 (19), 121 (23), 108 (21), 107 (100), 105 (17), 97 (24), 94 (20), 93 (37), 91 (34), 79 (21), 77 (16), 61 (10), 67 (18), 41 (23), 39 (11).

(±)-(IC*): (±)-(1S*,6R*,7R*)-1-methoxy-7,9-dimethyl-2-oxaspiro[5.5]undec-8-ene $^1$H-NMR (600 MHz, $C_6D_6$): δ selected signals 5.30-5.25 (m, 1H), 4.38 (s, 1H), 3.74-3.68 (m, 1H), 3.47-3.41 (m, 1H), 3.23 (s, 3H), 2.54-2.48 (m, 1H), 1.57 (s, 3H), 1.07 (dd, J=0.8, 7.2, 3H). $^{13}$C-NMR (150 MHz, $C_6D_6$): δ 130.9 (s), 126.7 (d), 102.9 (d), 58.6 (t), 54.4 (q), 36.7 (s), 32.7 (d), 26.6 (t), 25.2 (t), 25.2 (t), 23.3 (q), 20.9 (t), 17.0 (q).

GC-MS (EI): 210 (2), 195 (1), 179 (10), 178 (34), 163 (10), 150 (7), 135 (15), 122 (19), 121 (23), 108 (19), 107 (100), 105 (14), 97 (26), 94 (23), 93 (35), 91 (29), 79 (21), 77 (15), 61 (8), 67 (17), 41 (23), 39 (10).

(±)-(Id*): (±)-(1R*,6R*,7R*)-1-methoxy-7,9-dimethyl-2-oxaspiro[5.5]undec-8-ene $^1$H-NMR (600 MHz, $C_6D_6$): δ (selected signals) 5.30-5.27 (m, 1H), 4.16 (s, 1H), 3.72-3.66 (m, 1H), 3.53-3.47 (m, 1H), 3.23 (s, 3H), 2.09-2.01 (m, 2H), 1.57 (s, 3H), 0.93 (dd, J=7.2, 3H). $^{13}$C-NMR (150 MHz, $C_6D_6$): δ 130.6 (s), 126.9 (d), 103.8 (d), 59.2 (t), 54.2 (q), 38.2 (d), 36.9 (s), 26.8 (t), 25.6 (t), 21.9 (t), 21.9 (t), 23.3 (q), 15.9 (q).

GC-MS (EI): 210 (1), 195 (1), 179 (10), 178 (33), 163 (7), 150 (9), 135 (16), 122 (23), 121 (24), 108 (20), 107 (100), 105 (13), 97 (27), 94 (19), 93 (33), 91 (26), 79 (18), 77 (13), 61 (6), 67 (13), 41 (16), 39 (7).

(+)-(Id*): Olfactorily Inactive Enantiomer of the Main Diastereomeric Pair (±)-(Id*)

$^1$H-NMR (400 MHz, $CDCl_3$): δ 5.27-5.23 (m, 1H, H—C(8)=), 4.10 (s, 1H, H—C(1)), 3.71 (ddd, 1H, J=2.9, 10.8, 13.2, H—C(3)), 3.55 (ddt, 1H, J=1.5, 5.4, 11.0, H—C(3)), 3.36 (s, 3H, MeO), 1.97-1.71 (m, 5H), 1.68-1.61 (dm, J=14.2, 1H), 1.61 (s, 3H, MeC(9)=), 1.46-1.28 (m, 3H), 0.85 (d, J=7.1, 3 H, Me-C(7)). $^{13}$C-NMR (100 MHz, $CDCl_3$): δ 130.74 (s), 126.29 (d), 103.88 (d), 59.24 (t), 54.52 (q), 37.77 (d), 36.60 (s), 26.53 (t), 25.24 (t), 23.21 (q), 21.65 (t), 21.58 (t), 15.62 (q).

ORD: (25° C., c=1.010 in EtOH): $[\alpha]_D$: +180.3; $[\alpha]_{578}$: +213.6 (Hg); $[\alpha]_{405}$: +435 (Hg); $[\alpha]_{385}$: +570.5 (Hg).

GC-Threshold estimation: >250 ng (technical limit of the method)

Odour description: odorless.

(−)-(Id\*): Olfactorily Active Enantiomer of the Main Diastereomeric Pair (±)-(Id\*)

¹H-NMR (400 MHz, CDCl₃): δ 5.28-5.24 (br. m, 1H, H—C(8)=), 4.11 (s, 1H, H—C(1)), 3.72 (ddd, 1H, J=2.9, 10.8, 13.2, H—C(3)), 3.56 (ddt, 1H, J=1.4, 5.3, 10.9, H—C(3)), 3.37 (s, 3H, MeO), 1.98-1.72 (m, 5H), 1.69-1.62 (dm, J=13.8, 1H), 1.62 (s, 3H, MeC(9)=), 1.47-1.29 (m, 3H), 0.86 (d, J=6.9, 3 H, Me-C(7)). ¹³C-NMR (100 MHz, CDCl₃): δ 130.79 (s), 126.29 (d), 103.90 (d), 59.26 (t), 54.56 (q), 37.78 (d), 36.62 (s), 26.55 (t), 25.25 (t), 23.24 (q), 21.67 (t), 21.59 (t), 15.64 (q).

GC-MS (EI): 210 (1), 179 (12), 178 (38), 163 (9), 150 (10), 135 (18), 122 (24), 121 (25), 108 (19), 107 (100), 105 (13), 97 (29), 94 (18), 93 (32), 91 (27), 79 (17), 77 (13), 61 (9), 67 (14), 41 (21), 39 (10).

ORD (25° C., c=0.491 in EtOH): $[\alpha]_D$: −174; $[\alpha]_{546}$: −202 (Hg), $[\alpha]_{405}$: −409 (Hg), $[\alpha]_{365}$: −535 (Hg).

GC-Threshold: 7.2 ng

Odour description: fruity, cassis, grapefruit, juicy

The invention claimed is:

1. A compound according to formula (−)-(Id\*)

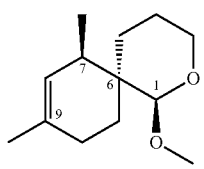

(−)-(Id\*)

wherein the compound shows negative specific rotation values.

2. An isomeric mixture comprising the compound as defined in claim 1 and the compound according to formula (+)-(Id\*)

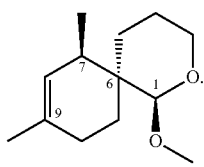

(+)-(Id\*)

3. The isomeric mixture according to claim 2, wherein the weight ratio of the compound according to formula (−)-(Id\*) and the compound according to formula (+)-(Id\*) is 1:1, and the isomeric mixture is a racemic mixture (±)-(Id\*)

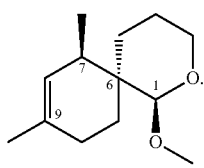

(±)-(Id\*)

(rac.)

4. A method of utilizing the compound of formula (−)-(Id\*) as defined in claim 1 as fragrance.

5. A method of improving, enhancing, or modifying a consumer product base by means of addition thereto of an olfactory acceptable amount of the compound of formula (−)-(Id\*) as defined in claim 1.

6. A perfumed article comprising as odorant the compound of formula (−)-(Id\*) as defined in claim 1 and a consumer product base.

7. The perfumed article according to claim 6 wherein the consumer product base is selected from the group consisting of: fine fragrance, household products, laundry products, body care products, cosmetic products, and air care products.

8. A fragrance composition perfume composition comprising the compound of formula (−)-(Id\*) as defined in claim 1 and a base material.

9. A fragrance composition perfume composition comprising the compound of formula (−)-(Id\*) as defined in claim 1, providing a cassis note to the composition.

10. A method of utilizing the isomeric mixture as defined in claim 2 as fragrance.

11. A method of utilizing the isomeric mixture as defined in claim 3 as fragrance.

12. A method of improving, enhancing, or modifying a consumer product base by means of addition thereto of an olfactory acceptable amount of the isomeric mixture as defined in claim 2.

13. A method of improving, enhancing, or modifying a consumer product base by means of addition thereto of an olfactory acceptable amount of the isomeric mixture as defined in claim 3.

14. A perfumed article comprising as odorant the isomeric mixture as defined in claim 2 and a consumer product base.

15. The perfumed article according to claim 14 wherein the consumer product base is selected from the group consisting of: fine fragrance, household products, laundry products, body care products, cosmetic products, and air care products.

16. A perfumed article comprising as odorant the isomeric mixture as defined in claim 3 and a consumer product base.

17. The perfumed article according to claim 16 wherein the consumer product base is selected from the group consisting of: fine fragrance, household products, laundry products, body care products, cosmetic products, and air care products.

18. A perfume composition comprising the isomeric mixture as defined in claim 2 and a base material.

19. A perfume composition comprising the isomeric mixture as defined in claim 3 and a base material.

20. A perfume composition comprising the isomeric mixture as defined in claim 2, providing a cassis note to the composition.

21. A perfume composition comprising the isomeric mixture as defined in claim 3, providing a cassis note to the composition.

\* \* \* \* \*

UNITED STATES PATENT AND TRADEMARK OFFICE
CERTIFICATE OF CORRECTION

PATENT NO. : 12,378,214 B2
APPLICATION NO. : 17/615301
DATED : August 5, 2025
INVENTOR(S) : Thierry Granier et al.

Page 1 of 1

It is certified that error appears in the above-identified patent and that said Letters Patent is hereby corrected as shown below:

In the Claims

Claim 8 (Column 12, Line 16) should recite "A perfume composition comprising".

Claim 9 (Column 12, Line 19) should recite "A perfume composition comprising".

Signed and Sealed this
Thirtieth Day of September, 2025

John A. Squires
*Director of the United States Patent and Trademark Office*